United States Patent
Takahashi et al.

(10) Patent No.: US 6,479,170 B2
(45) Date of Patent: Nov. 12, 2002

(54) ELECTRODEPOSITED COPPER FOIL, METHOD OF INSPECTING PHYSICAL PROPERTIES THEREOF, AND COPPER-CLAD LAMINATE EMPLOYING THE ELECTRODEPOSITED COPPER FOIL

(75) Inventors: Naotomi Takahashi; Yutaka Hirasawa, both of Ageo (JP)

(73) Assignee: Mitsui Mining & Smelting Co., Ltd. (JP)

( * ) Notice: Subject to any disclaimer, the term of this patent is extended or adjusted under 35 U.S.C. 154(b) by 0 days.

(21) Appl. No.: 09/755,772

(22) Filed: Jan. 5, 2001

(65) Prior Publication Data
US 2001/0008091 A1 Jul. 19, 2001

(30) Foreign Application Priority Data
Jan. 6, 2000 (JP) ......................................... 2000-001122

(51) Int. Cl.$^7$ ......................... B32B 15/20; G01N 33/20
(52) U.S. Cl. ............................. 428/674; 73/789; 73/826; 73/866; 148/686; 428/606; 428/607; 428/935
(58) Field of Search ................................ 428/674, 606, 428/607, 935, 686; 73/789, 826, 866

(56) References Cited
U.S. PATENT DOCUMENTS
6,132,887 A * 10/2000 Clouser et al. ............. 428/606

FOREIGN PATENT DOCUMENTS
EP 0 207 224 B2 3/1999 ............ C25D/1/04

* cited by examiner

Primary Examiner—Robert R. Koehler
(74) Attorney, Agent, or Firm—Jenkens & Gilchrist

(57) ABSTRACT

The present invention provides an electrodeposited copper foil which solves problems of electrodeposited-copper-clad laminates to which the foil has been incorporated, such as bow, twist, and poor dimensional stability, and a method of inspecting an electrodeposited copper foil so as to assure the quality of the foil. In the invention, there is employed an electrodeposited copper foil which recrystallizes by heating at low temperature during production of a copper-clad laminate employing an electrodeposited copper foil and which exhibits an elongation as high as 18% or more in an atmosphere of 180° C., wherein the maximum rate of decrease in maximum tensile strength falls within the aging time ranging from 5 to 10 minutes in a process in which tensile strength decreases as time elapses during aging in an atmosphere at 170° C., and the change in tensile strength in a knick portion shown in a {tensile strength} vs. {aging time} curve which is drawn in an x–y plane and which has a knick portion is 3 kg/mm$^2$ or more, the x-axis representing aging time and the y-axis representing tensile strength.

3 Claims, 6 Drawing Sheets

Aging conditions    170°C × 5 minutes

Aging conditions    170°C × 10 minutes

Aging conditions 170°C × 5 minutes

Aging conditions 170°C × 10 minutes

Aging conditions    180°C × 5 minutes

Aging conditions    180°C × 10 minutes (a) Aging temperature 170°C (b) Aging temperature 180°C Electroforming step A Surface-treatment step B

ELECTRODEPOSITED COPPER FOIL, METHOD OF INSPECTING PHYSICAL PROPERTIES THEREOF, AND COPPER-CLAD LAMINATE EMPLOYING THE ELECTRODEPOSITED COPPER FOIL

TECHNICAL FIELD

The present invention relates to electrodeposited copper foil; to a method of evaluating physical properties of the electrodeposited copper foil; and to a copper-clad laminate employing the electrodeposited copper foil.

BACKGROUND ART

Conventionally, copper foil has been employed as a material for producing printed wiring boards, which are widely used in the electric and electronics industries. In general, electrodeposited copper foil is bonded, through hot-pressing, onto an electrically insulating polymer material substrate such as a glass-epoxy substrate, a phenolic polymer substrate, or polyimide, to thereby form a copper-clad laminate, and the thus-prepared laminate is used for producing printed wiring boards.

In conventionally carried out hot-pressing, a copper foil, a prepreg (substrate) which is cured into a B-stage, and mirror plates serving as spacers are laid-up in a multilayered manner, and the copper foil and the prepreg are hot-press-bonded at high temperature and pressure (hereinafter the step may be referred to as "batch-press-lamination"), to thereby produce a copper-clad laminate.

However, in recent years, reducing the production costs of commercial copper foil products has been an essential issue for maintaining the global competitiveness in the electric and electronics industries. Thus, there is intense demand for reduction in production costs and, further, reduction in the price of printed wiring boards serving as principal components of electronic apparatus.

To meet the demand, a variety of efforts have been made to reducing costs of copper-clad laminates and electrodeposited copper foil, which are intermediate products for producing printed wiring boards. For example, instead of FR-4, CEM-3 has been employed as a copper-clad laminates, and a continuous lamination method has been employed so as to remarkably enhance productivity.

However, the aforementioned alteration in material and method of production results in adverse effects on copper-clad laminates, which effects have never been observed. Thus, an electrodeposited copper foil, serving as a basic material, is required to have characteristics to overcome the adverse effects. In particular, the problems which arise after an electrodeposited copper foil has been bonded to a substrate include bow or warpage, twist, and poor dimensional stability of the copper-clad laminates.

As one solution to the aforementioned problems, Japanese Patent Application Laid-Open (kokai) No. 2-258337 discloses employment of an electrodeposited copper foil exhibiting excellent high-temperature elongation (HTE) characteristics (hereinafter referred to as "S-HTE foil"); i.e., an elongation as high as more than 10% in an atmosphere of 180° C. Although attempts have been made to solve the aforementioned problems by controlling tensile strength in an atmosphere of 180° C., as disclosed in Japanese Patent Application Laid-Open (kokai) No. 5-24152, the problems have not yet been solved completely.

SUMMARY OF THE INVENTION

Figure 1:
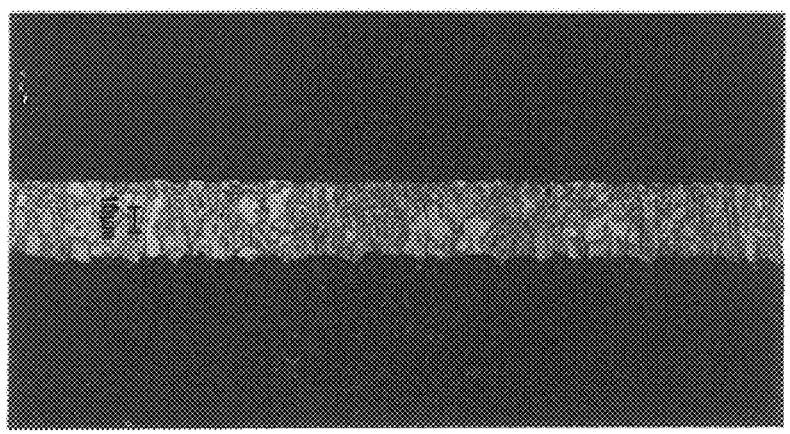
FIGS. 1 to 3 show optical-microscopic images of recrystallization structures of electrodeposited copper foil specimens which are employed to describe the present invention.
Figure 1:
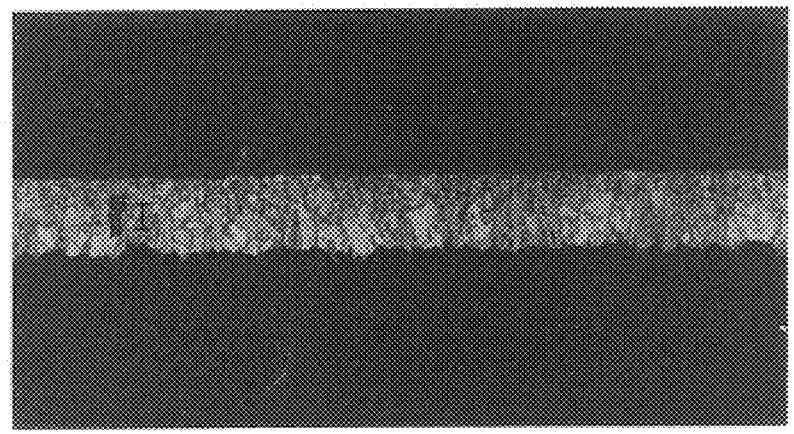

In view of the foregoing, the present inventors have conducted extensive studies, and have found that no essential correlation is observed between the progress of recrystallization, and elongation or tensile strength of electrodeposited copper foil in an atmosphere of approximately 180° C. where recrystallization is progressing—at this temperature, an electrodeposited copper foil having excellent high-temperature elongation properties generally recrystallizes.

The present inventors had previously identified factors useful for controlling the extent of recrystallization during the production of electrodeposited copper foil. However, control attained on the basis of such factors from the viewpoints of the electrochemical process and mass-production considerably increases production costs. Thus, the inventors have determined that implementation of the above control is currently difficult.

Even though a production step for drum foil such as S-HTE foil is modified so as to omit implementation of the aforementioned control, those S-HTE foil products which make no contribution to reducing bow and twist or to improving the dimensional stability are unavoidably produced to a certain degree, due to difficulty in controlling the electrochemical production method per se. Briefly, such S-HTE foil products are unavoidably produced in the production of electrodeposited copper foil. In order to detect such S-HTE copper foil products, the present inventors have elucidated, by employing a copper-clad laminate of a CEM-3 type prepreg that readily generates bow and twist, that electrodeposited copper foil which can reduce bow and twist and improve the dimensional stability of a copper clad laminate has a specific range of qualities. The present invention has been accomplished on the basis of these findings.

Accordingly, in one aspect of the present invention, there is provided an electrodeposited copper foil which recrystallizes by heating at low temperature during production of a copper-clad laminate employing in electrodeposited copper foil and which exhibits an elongation as high as 18% or more in a hot atmosphere of 180° C., wherein the maximum rate of decrease in maximum tensile strength falls within an aging time ranging from 5 to 10 minutes in a process in which tensile strength decreases as time elapses during aging in a hot atmosphere at 170° C. and the change in tensile strength in a knick portion in a {tensile strength}vs. {aging time}curve which is drawn in an x–y plane and which has a knick portion is 3 kg/mm$^2$ or more, the x-axis representing aging time and the y-axis representing tensile strength.

The expression "a low-temperature annealable electrodeposited copper foil which recrystallizes by heating at low temperature during production of a copper-clad laminate employing an electrodeposited copper foil" refers to an HTE foil classified as Grade 3 in accordance with the standards of the IPC (Institute for Interconnecting and Packaging Electronic Circuits).

For the sake of simplicity, the classification of electrodeposited copper foils will be described. According to the IPC standards, electrodeposited copper foils are classified as Grade 1 to Grade 3 on the basis of basic physical properties such as elongation and tensile strength. Copper foil designated by Grade 1 is standard electrodeposited copper foil, and copper foil designated by Grade 2 is high ductile electrodeposited copper foil. These days, among persons having ordinary skill in the art, electrodeposited copper foils belonging to Grades 1 and 2 are generally called standard electrodeposited copper foils. Electrodeposited copper foil belonging to Grade 3 is generally called HTE foil. HTE foil generally refers to copper foil exhibiting high temperature elongation of 3% or more in an atmosphere at 180° C. HTE foil is completely different from standard copper foils belonging to Grades 1 and 2, since the standard copper foils exhibit a high temperature elongation less than 2%.

In recent manufacture of printed wiring boards, copper foils belonging to Grade 3 are further classified into two distinct categories; i.e., electrodeposited copper foils exhibiting a high temperature elongation of approximately 3% to 18% (hereinafter simply referred to as HTE foils) and electrodeposited copper foils exhibiting a high temperature elongation more than approximately 18% to 50% (throughout the present description, these foils are simply referred to as S-HTE foils). These two types of foils are employed in accordance with applications.

The basic difference between HTE foil and S-HTE foil lies in the characteristics of deposited crystals, even though both of these foils comprise electrodeposited copper having a purity of approximately 99.99%. During a process for producing copper-clad laminates, an electrodeposited copper foil is hot-pressed so as to be laminated with a substrate, by being subjected to a heat treatment of at least 170–180° C. for approximately 60 minutes. Through observation under an optical microscope of the grain structure of the foils after completion of heating, no recrystallization is observed in HTE foil, but recrystallization is observed in S-HTE foil.

The difference is considered to be attributed to production conditions of the foils. Briefly, production conditions during electroforming, such as composition of a solution, concentration of a solution, method for filtering a solution, solution temperature, additives, and current density, are modified in order to control physical properties of copper foils. This may cause variation in crystallographic properties of deposited crystals. Particularly, copper foil material which readily permits recrystallization tends to accumulate in crystals dislocations more densely as compared with copper foil materials which do not readily permit recrystallization. The dislocations are not immobilized tightly, and immediately undergo rearrangement under application of a small amount of heat, thereby possibly causing recrystallization readily.

The progress of recrystallization of electrodeposited copper foil completely depends on the aging temperature and time. In order to determine the progress of recrystallization, no other way can be conceived than observation of the grain structure of the copper foil. The currently employed method includes cutting an electrodeposited copper foil which has been aged for a predetermined time; polishing a resultant cross-section; and etching the cross-section by use of an etchant such as a ferric chloride solution, to thereby perform observation. Since the electrodeposited copper foil to be observed has a thickness of 100 μm or less, observation of the cross-sectional grain structure thereof is difficult. Only persons skilled in the art; particularly, those skilled in polishing and etching techniques, can carry out the observation. FIG. 1 shows a change in the grain structure of an S-HTE foil before and after aging (heating) for a predetermined time.

Figure 2:
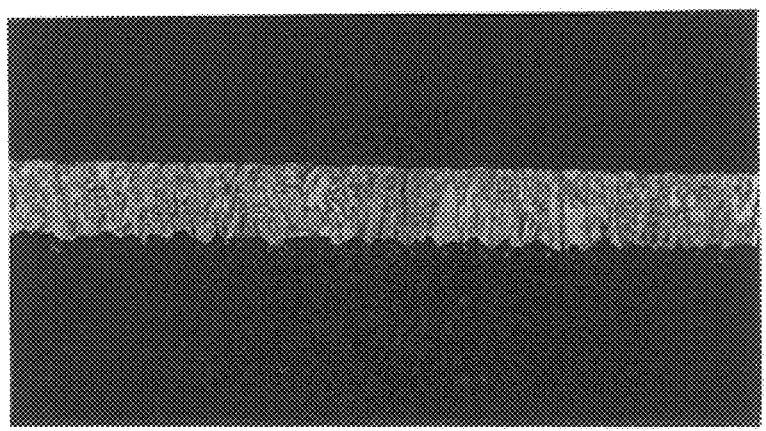
Figure 2:
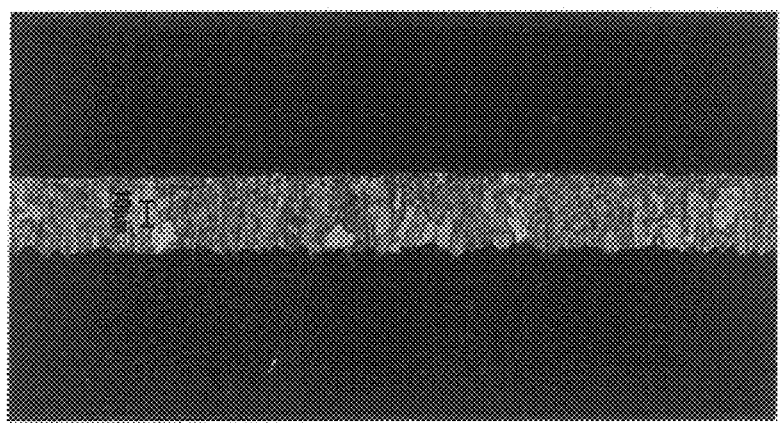
Figure 3:
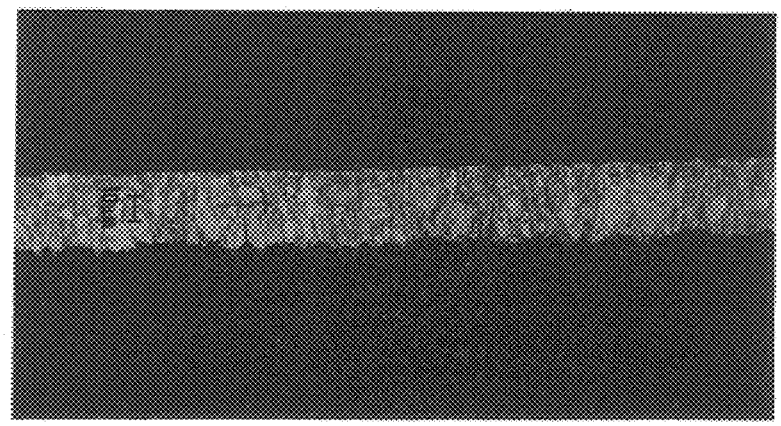
Figure 3:
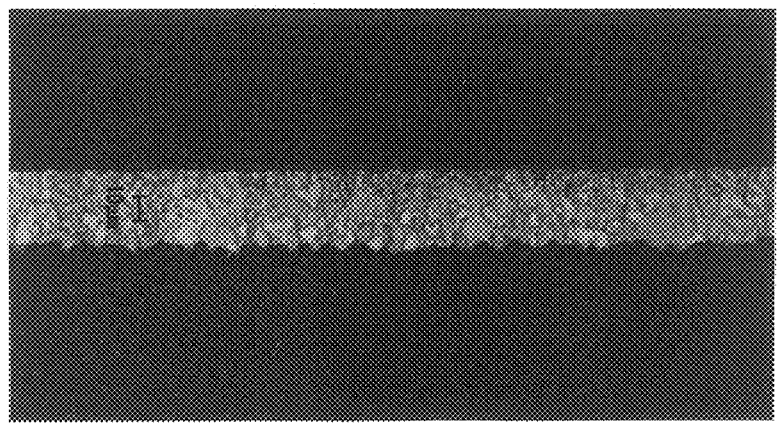

The S-HTE foil having grain structures shown in FIG. 1 is a typical copper foil which contributes to reducing bow and twist and to improving the dimensional stability of a copper-clad laminate employing the copper foil. In contrast, the S-HTE foil having grain structures shown in FIG. 2 is a typical copper foil which does not contribute to reducing bow and twist or to improving the dimensional stability of a copper-clad laminate employing the copper foil. The grain structures of cross-sections shown in FIGS. 1 and 2 are those observed after aging at 170° C., whereas the grain structures shown in FIG. 3 are those observed after aging at 180° C. In general, recrystallizable electrodeposited copper foil undergoes recrystallization very rapidly at 180° C. or higher. The grain structures shown in FIG. 3 exhibit results of more rapid recrystallization as compared with grain structures shown in FIGS. 1 and 2.

In recent years, a variety of techniques for producing copper-clad laminates have been employed in an attempt to effect cost reductions. In conventional batch-press-forming, sufficient heat; i.e., approximately 180° C., to cause sufficient recrystallization, and sufficient pressure can be provided during hot-pressing. Thus, bow, twist, and dimensional instability of the produced copper-clad laminates can be prevented. In addition, as disclosed in Japanese Patent Application Laid-Open (kokai) No. 5-243698, the dimensional stability of copper-clad laminates can be further improved by heating again after completion of press-forming. In the above case, however, the increased number of steps is disadvantageous.

Another example method of producing copper-clad laminates is a continuous lamination method, which comprises bonding an electrodeposited copper foil and a substrate by applying roll pressure; hardening a resin of the substrate while the resultant laminate runs in a hardening furnace; and cutting the hardened laminate to desired dimensions. In this method, only a small quantity of heat imparted to a copper foil in a hardening furnace is required as compared with a conventional press-forming method, since the resin employed in continuous lamination can be quickly hardened by a small quantity of heat. As a result, an interior portion of the electrodeposited copper foil might remain insufficiently recrystallized.

As is clear from the foregoing, S-HTE foil products which contribute to reducing bow and twist and to improving dimensional stability should also recrystallize quickly even at a low temperature. Although attempts have been made to reduce bow and twist and to improve dimensional stability of a copper-clad laminate by controlling elongation and tensile strength in an atmosphere of 180° C., resolution has still not been completely attained. This is because the progress of recrystallization has not yet been taken into consideration. Actually, so far as the investigation by the present inventors is concerned, no essential correlation has been observed between the progress of recrystallization, and elongation or tensile strength of electrodeposited copper foil in a hot temperature. Particularly, elongation and tensile strength at 180° C. have no clear correlation with the extent of recrystallization, since recrystallization is progressing simultaneously with measurement at 180° C.

In consideration of the above description, the present inventors have determined that an electrodeposited copper foil which contributes to reducing bow and twist and to improving the dimensional stability of copper-clad laminates cannot be identified by measuring the physical properties of the electrodeposited copper foil at approximately 180° C., at which temperature all S-HTE foil products readily recrystallize. FIG. 1 shows a cross-sectional photographic image, obtained after termination of aging at 170° C., of a grain structure of an S-HTE foil which can reduce bow and twist and improve dimensional stability of a copper-clad laminate employing CEM-3. FIG. 2 shows a cross-sectional photographic image, obtained after termination of aging at 170° C., of a grain structure of an S-HTE foil which cannot reduce bow and twist or improve dimensional stability of a copper-clad laminate employing CEM-3. As is clear from the grain structures shown in FIG. 1, recrystallized grains generated in the grain structure of electrodeposited crystals are grown in a longitudinal direction. The grain size distribution of the recrystallized grains shown in FIG. 1 is more uniform than that of the recrystallized grains shown in FIG. 2. In addition, recrystallization occurs more rapidly in the case of FIG. 1 than in the case of FIG. 2. As is also clear from FIGS. 1 and 2, as compared with the grains shown in FIG. 2, recrystallized grains shown in FIG. 1 have a smaller grain size and are more densified.

FIG. 3 shows a cross-sectional photographic image, obtained after termination of aging at 180° C., of a grain structure of an S-HTE foil. As is clear from FIG. 3, recrystallization is completed within 10 minutes, which differs from the case of aging at 170° C. In this case, the employed S-HTE foil has already been shown in FIG. 2 and cannot reduce bow and twist or improve dimensional stability of a copper-clad laminate employing CEM-3. A similar grain structure of recrystallized grains is observed in an S-HTE foil which has already been shown in FIG. 1 but is not illustrated herein. Thus, the two types of S-HTE foil products cannot be distinguished from each other. As described above, all S-HTE foil products readily recrystallize by aging at 180° C. When S-HTE foil is aged at 180° C., interlot differences in recrystallization rate and differences in the size of recrystallized grains are difficult to identify.

With reference to FIGS. 1 to 3, the present inventors consider that evaluation of the extent of recrystallization occurring after aging at 170° C. is more useful for determining the progress of recrystallization of an S-HTE than evaluation at 180° C. The present inventors have further elucidated that the profile of a {tensile strength} vs. {aging time} curve which is obtained by measuring the tensile strength of a copper foil after aging at 170° C. for a predetermined time varies greatly in accordance with the nature of the copper foil; i.e., whether or not the copper foil can reduce bow and twist and improve dimensional stability of a copper-clad laminate.

Figure 4:
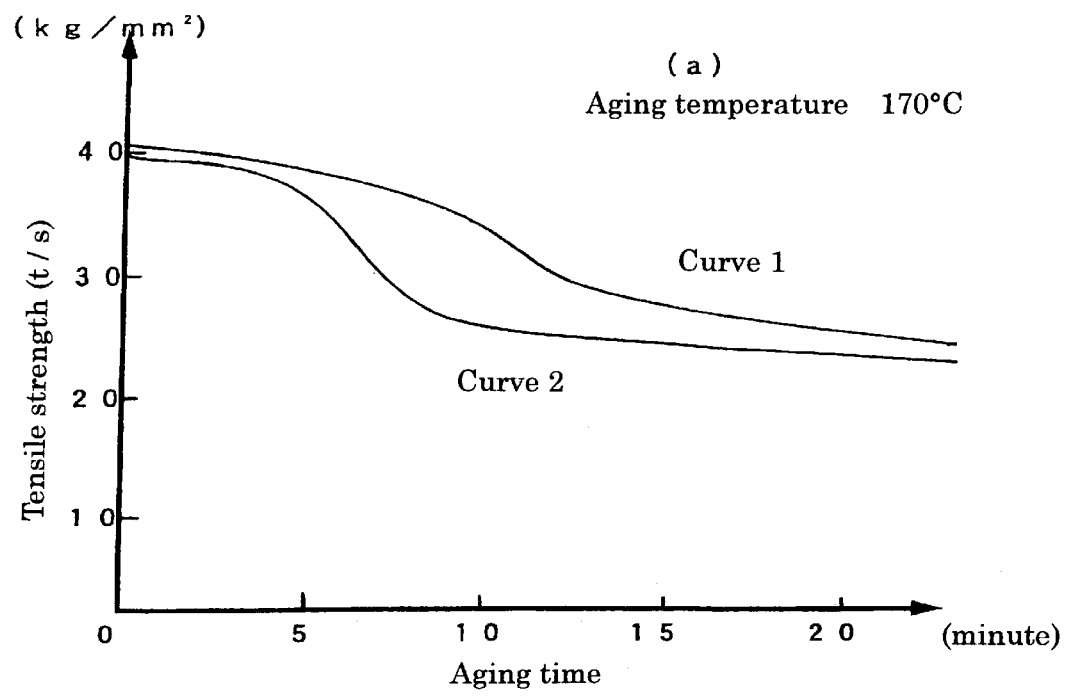
FIG. 4 shows relationships between aging time and actually measured tensile strength of the electrodeposited copper foil specimens.
Figure 4:
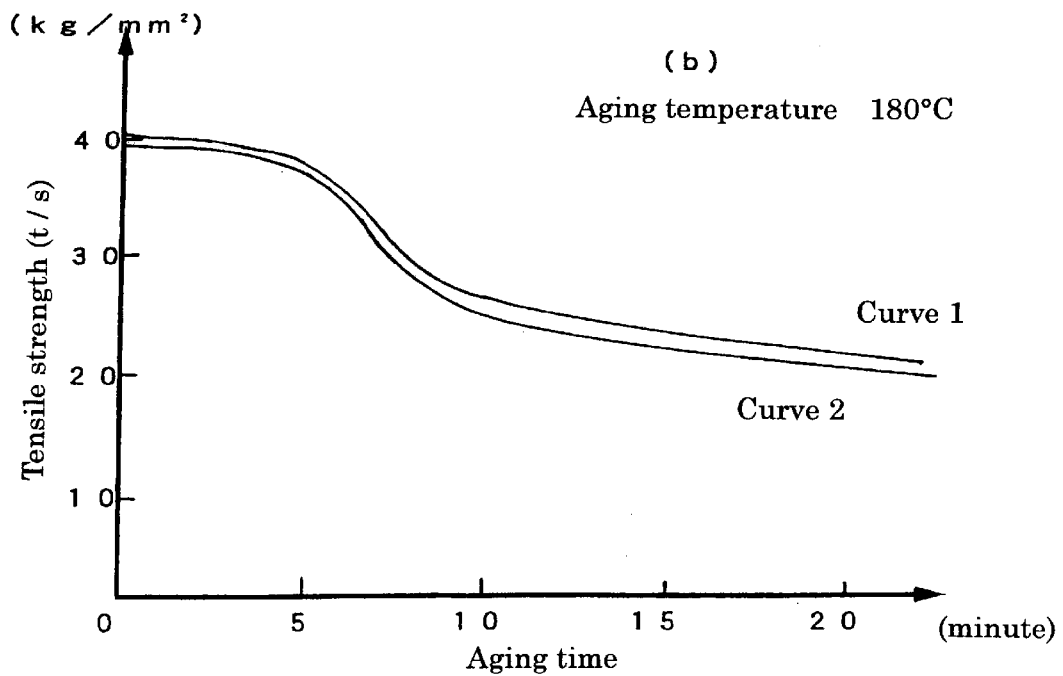

FIG. 4(a) shows {tensile strength} vs. {aging time} curves, obtained by measuring after aging at 170° C., of two S-HTE foil specimens having different recrystallization rates. FIG. 4(b) shows similar {tensile strength} vs. {aging time} curves, obtained by measuring after aging at 180° C. The tensile strength was measured in accordance with IPC-TM-650 standards. Specifically, the maximum tensile strength of a specimen was measured at room temperature after the specimen had undergone aging for a predetermined time. Accordingly, the tensile strength represented by the y-axis of FIGS. 4(a) and 4(b) or represented below in FIG. 5 refers to the maximum tensile strength obtained in the aforementioned manner. As shown in these Figs., each curve has a knick portion where the gradient of the curve drastically changes within the aging time range of 5 minutes to 10 minutes. However, the difference in profile between two curves is clearer in the case of aging at 170° C. than in the case of aging at 180° C.

In FIGS. 4(a) and 4(b), curve 1 represents the tensile behavior of an S-HTE foil which has a slow recrystallization rate and which cannot reduce bow, twist, or other types of deformation of a copper-clad laminate. Curve 2 represents the tensile behavior of an S-HTE foil according to the present invention. As is clear from FIGS. 4(a) and 4(b), identification of the interlot differences in physical properties of copper foil is performed more easily in the case of aging at 170° C. than in the case of aging at 180° C.

The present inventors have carried out further studies, and have found that when the change in tensile strength of a copper foil over a knick portion of a {tensile strength} vs. {aging time} curve of 170° C. aging is 3 kg/mm$^2$ or more, such a copper foil can further reduce bow and twist and improve dimensional stability of a copper-clad laminate. The term "knick portion of a {tensile strength} vs. {aging time} curve" will next be described in detail with reference to FIG. 5.

Figure 5:
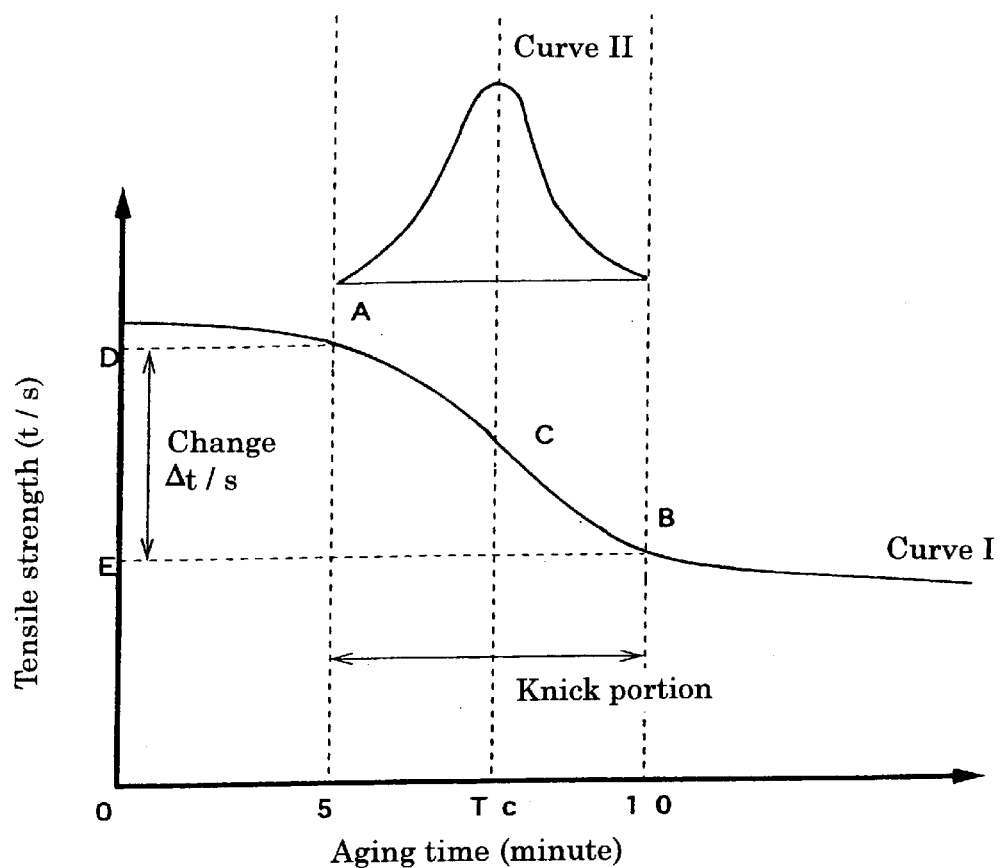
FIG. 5 shows a model relationship between aging time and tensile strength of an electrodeposited copper foil.

Three points represented by A, B, and C are shown in FIG. 5. The aforementioned knick portion refers to the portion which is defined by points A and B and, when considered from the overall curve of {tensile strength} vs. {aging time} in which the differential coefficient of the curve changes drastically. Accordingly, "the change in tensile strength in a knick portion" is defined by the difference, represented by Δt/s, between the tensile strength at point A (corresponding to point D in FIG. 5) and that at point B (corresponding to point E in FIG. 5).

The aging time at which the rate of decrease in maximum tensile strength reaches its maximum was obtained in the following manner. Specifically, differential coefficients of the knick portion (between points A and B) of the {tensile strength} vs. {aging time} curve (curve I) were plotted to draw curve II shown in FIG. 5. By use of the turning point—corresponding to point C in FIG. 5 of curve II, which is fairly representative of a normal distribution (Gaussian distribution), the aging time at which the rate of decrease in maximum tensile strength reaches maximum was determined. If point C falls within the time range of 5 minutes to 10 minutes, the aging time falls within the scope of the present invention. In FIG. 4(a), the point of curve 1 related to aging at 170° C. corresponding to point C falls outside the aging time range; i.e., 5 minutes to 10 minutes. Thus, a copper foil having a tensile profile represented by curve 1 falls outside the scope of claim 1 of the invention.

As described above, there can be determined the conditions that must pertain so that S-HTE copper foil can absolutely reduce bow and twist and improve the dimensional stability of a copper clad laminate. The present inventors further consider that establishment of a method of inspecting S-HTE foil so as to ensure the quality of commercial S-HTE foil products is an essential issue.

Accordingly, in a second aspect of the prevention, there is provided a method of inspecting an electrodeposited copper foil, in terms of quality, comprising cutting an electrodeposited copper foil of one production lot so as to prepare two strip specimens having dimensions of 1 cm×10 cm; subjecting one specimen to aging at 170° C. for 5 minutes and the other specimen to aging at 170° C. for 10 minutes; subsequently cooling the specimens to room temperature; subsequently setting each specimen into a tensile tester; applying a tensile force at a rod speed of 50 mm/minute; and measuring the maximum tensile strength of each specimen so as to confirm that the difference between the two values is 3 kg/mm$^2$ or more.

Conventionally, high-temperature inspection of copper foil; i.e., evaluation of physical properties of copper foil per se, has been carried out in an atmosphere at 180° C., which contrasts sharply with the practice whereby the heat resistance of particular printed wiring boards has been evaluated in accordance with the UL 796 Safety Standards, which are common standards among U.S. insurance companies. However, as mentioned above, physical properties of S-HTE foil evaluated in an atmosphere at 180° C. cannot be employed in inspection of S-HTE foil for determining the progress of recrystallization. Thus, the present inventors have determined that the tensile strength of an S-HTE copper foil which has undergone aging at 170° C. should be employed as an index for inspection.

The present have measured the tensile strength of over 300 lots of specimens so as to establish the inspection method. Specifically, the inventors have measured bow, twist, and the dimensions of copper-clad laminates employing CEM-3, and have confirmed that the copper foil of the invention can reduce bow and twist and improve the dimensional stability of a copper-clad laminate and that the method of inspection is appropriate for inspecting electrodeposited copper foil.

As defined in the first aspect of the invention, an electrodeposited copper foil which can reduce bow and twist and improve dimensional stability of a copper-clad laminate satisfies two conditions; i.e., (1) the maximum rate of decrease in maximum tensile strength falls within the aging time ranging from 5 to 10 minutes and (2) the change in tensile strength in a knick portion shown in a {tensile strength}vs. {aging time}curve which is drawn in an x–y plane and which has a knick portion is 3 kg/mm$^2$ or more, the x-axis representing aging time and the y-axis representing tensile strength.

In practice, when 300 or more lots of copper foil products had been inspected in the aforementioned manner, most of the copper foil products which could reduce bow and twist and improve the dimensional stability of a copper-clad laminate exhibited a change in tensile strength of 3 kg/mm$^2$ or more within a time range of aging of 5 minutes to 10 minutes. Thus, the inventors have considered, on the basis of experimental results, that bow and twist of a copper clad laminate can be reduced and the dimensional stability thereof can be improved when the difference between the tensile strength at an aging time of 5 minutes and that at an aging time of 10 minutes is 3 kg/mm$^2$ or more.

In another aspect of the present invention, there is provided a copper-clad laminate employing an electrodeposited copper foil of the first aspect of the invention. By employing the electrodeposited copper foil of the invention, bow and twist of a copper-clad laminate; particularly, bow and twist of a copper-clad laminate employing a CEM-3 substrate, can be reduced and the dimensional stability thereof can be improved. Thus, patterning accuracy of a resist and etching accuracy during the etching process can be improved, thereby facilitating production of fine circuits from copper clad laminate.

EXAMPLES

Figure 6:
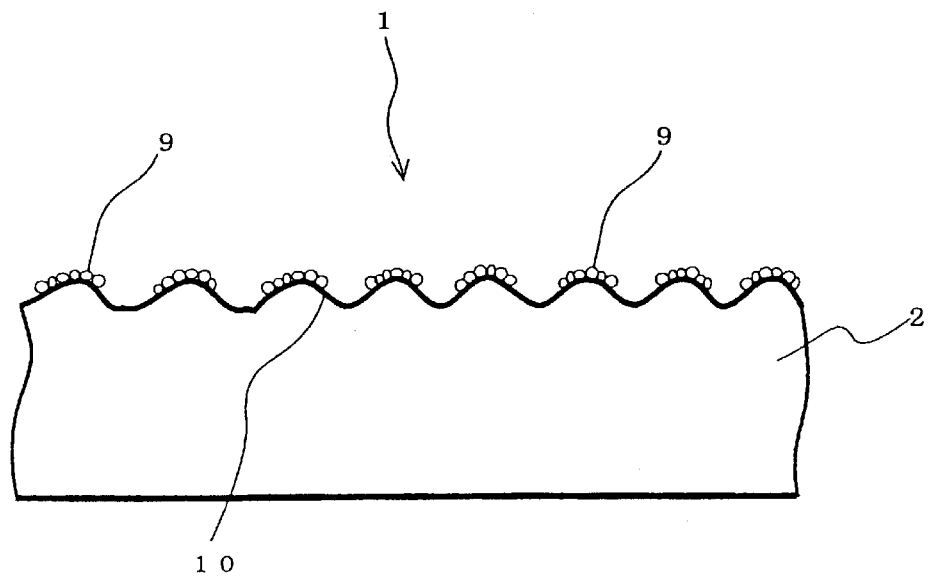
FIG. 6 is a schematic cross-sectional view of an electrodeposited copper foil.
Figure 7:
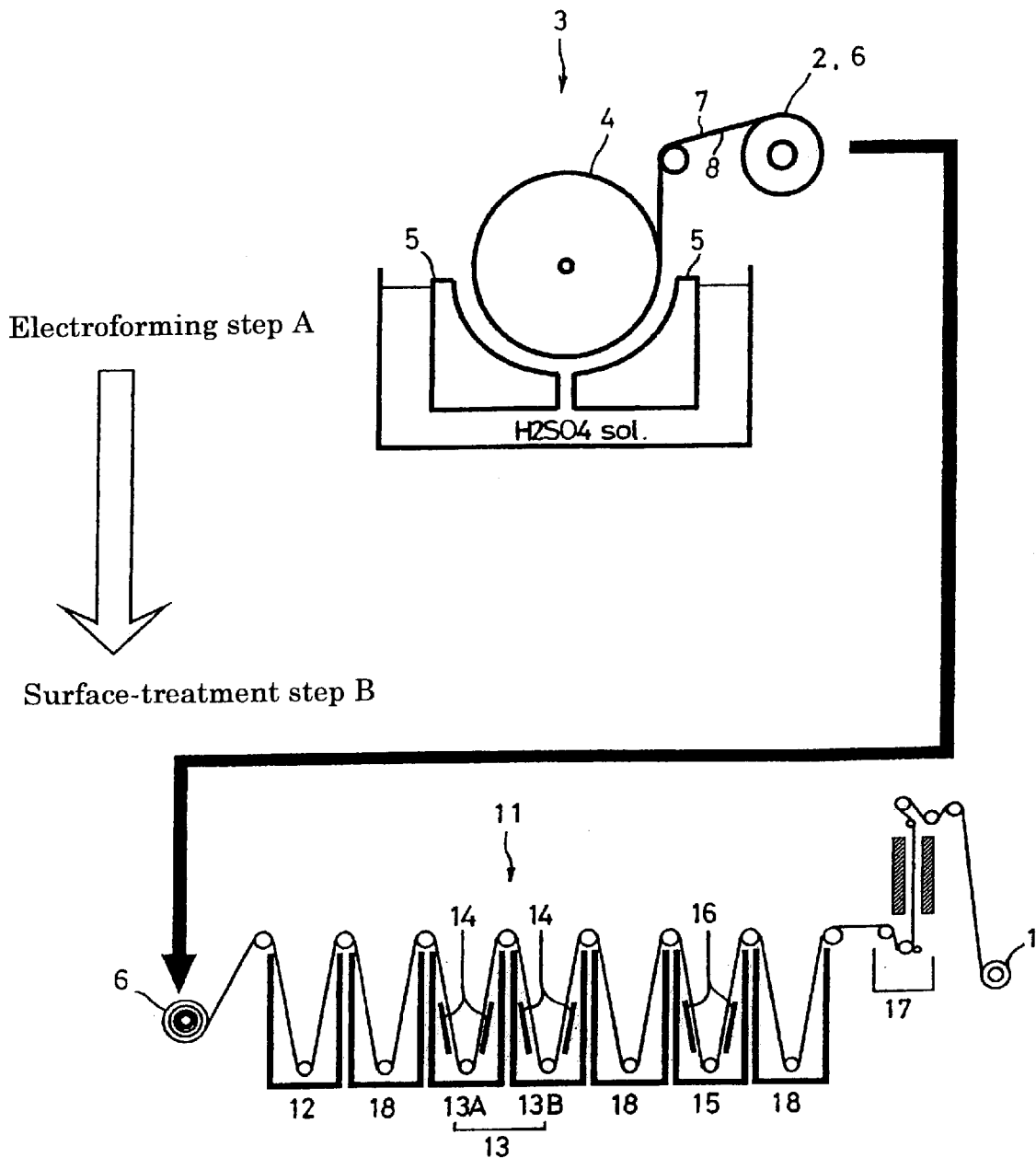
FIG. 7 shows a schematic view of production steps for an electrodeposited copper foil.

The present invention will next be described in more detail by way of example. Specifically, the method of producing an electrodeposited copper foil according to the present invention will be described with reference to FIG. 6 showing a cross-sectional view of an S-HTE copper foil 1 and FIG. 7 showing the production steps for the copper foil. In addition, copper-clad laminate CEM-3 were produced from an electrodeposited copper foil produced through the method, and bow, twist, and dimensional stability were evaluated. The results will be shown hereunder. It should be noted that in FIG. 6 layers which are difficult to depict, such as an anti-corrosion layer, are not shown, for the sake of simplicity.

In general, electrodeposited copper foil is produced through an electroforming step A and a surface-treatment step B. An S-HTE copper foil 1 according to the present invention is also produced in the same manner.

Firstly, the electroforming step A is described. In the electroforming step A, a bulk copper layer 2 of the electrodeposited copper foil 1 is produced. The electrodeposited copper foil serves as an electrical conductor after it has been processed into a printed wiring board. An electroforming cell 3 comprises a rotating drum cathode 4 and a lead anode 5 which faces the cathode 4 so as to surround the drum cathode. In practice, a copper sulfate solution is fed into a space defined by the rotatable drum cathode and the lead anode, to thereby electrolyze, and copper is deposited on the drum surface of the rotating drum cathode 4. The thus-deposited copper forms a copper foil, which is continuously peeled from the rotating drum cathode 4 and rolled up. By controlling the characteristics of the bulk copper layer 2 produced during the electroforming step A, the grade of the produced copper foil is determined.

An acidic solution of copper sulfate comprising copper sulfate ($CuSO_4.5H_2O$) (280–360 g/l) and sulfuric acid (100–150 g/l) is employed as an electrolyte for the electroforming step A. Electroforming is continuously carried out at a solution temperature of approximately 50° C. and at a current density of 50–100 A/dm$^2$, to thereby produce an S-HTE-copper foil. In this Example, a solution comprising copper sulfate ($CuSO_4.5H_2O$) (360 g/l) and sulfuric acid (150 g/l) was electrolyzed at a solution temperature of 49° C. and at a current density of 100 A/dm$^2$, thereby producing the bulk copper layer 2 for producing an electrodeposited copper foil having a nominal thickness of 18 $\mu$m.

The electrolyte employed for producing the S-HTE copper foil 1 is characterized in that the electrolyte is subjected to activated-carbon treatment prior to electroforming and that electroforming is carried out within 20 minutes after completion of activated-carbon treatment. The conditions of activated-carbon treatment are as follows: the amount of activated carbon brought into contact with the electrolyte is approximately 0.5–5.0 g to 1 liter of the electrolyte, and the contact time is approximately 20 seconds.

Thus, in the electroforming step A, the bulk copper layer 2 formed of an S-HTE copper foil which has not been subjected to surface any treatment is obtained. For the sake of simplicity, a copper foil exclusively formed of the bulk copper layer 2 is referred to as a "drum foil 6." Since the drum foil 6 has not been subjected to any surface treatment, such as anti-corrosion treatment, immediately after undergoing electrodeposition the copper has a highly activated surface which readily undergoes oxidation by oxygen contained in the air.

The surface of the drum foil 6 which is peeled from the rotating drum cathode 4 is shiny and smooth, since the mirror-polished surface of the rotating cathode is transferred to the foil surface. The thus-obtained surface is called a shiny side 7. In contrast, the surface configuration of the other surface, on which copper is electrodeposited, is rough, since the growth rate of copper crystals varies depending on the deposited crystal plane. Thus, this surface is called a matte side 8. The matte side 8 serves as a surface onto which an insulating material is bonded during production of a copper-clad laminate.

Subsequently, in the surface-treatment step B the drum foil 6 is subjected to surface treatment, including nodular treatment and anti-corrosion treatment of a matte side 8. The matte side 8 is subjected to nodular treatment; i.e., the drum foil is subjected to electroforming in a copper sulfate solution with a current under conditions for forming burnt deposits, to thereby form copper microparticles 9 on the matte side 8 so as to provide a rough surface. Immediately after the deposition, the foil is subjected to seal plating with a current under conditions for level plating, to thereby prevent release of deposited copper microparticles 9. Thus, the matte side 8 onto which copper microparticles 9 are deposited is hereinafter referred to as a "nodular-treated side 10."

Subsequently, in the surface-treatment step B, the nodular-treated drum foil 6 is subjected to anti-corrosion treatment in which both sides of the drum foil 6 are treated with coatings such as zinc, a zinc alloy, or a chromium-containing plating. The thus-treated foil is dried and rolled, to thereby produce an S-HTE copper foil to serve as a commercial product. The surface treatment will next be described in more detail.

In the surface-treatment step B, the drum foil 6 is unwound from a foil roll and travels, in a winding manner, in the surface-treatment apparatus 11 as shown in FIG. 7, which is a schematic cross-sectional view. Hereinafter, production conditions will be described with reference to the apparatus 11, wherein a variety of baths are continuously arranged in-line.

Firstly, the drum foil 6 taken from the foil roll is transferred into a pickling bath 12 filled with a diluted sulfuric acid solution having a concentration of 150 g/l and a solution temperature of 30° C. The foil is immersed for 30 seconds, so as to remove oily matter and excessive surface oxide film from the surface of the drum foil 6.

After the drum foil 6 has been treated in the pickling bath 12, the foil is transferred into nodular-treatment baths 13 in order to form copper microparticles 9 on the surface of the drum foil 6. The treatment carried out in the nodular-treatment baths 13 involves depositing copper microparticles 9 on one surface of the drum foil 6 (in bath 13A) and seal-plating so as to prevent release of the copper microparticles 9 (in bath 13B).

In the bath 13A for depositing copper microparticles 9 on the drum foil 6, a copper sulfate solution (sulfuric acid concentration of 100 g/l, copper concentration of 18 g/l, temperature 25° C.) is employed, and electroplating is carried out for 10 seconds under conditions for forming burnt deposits at a current density of 10 A/dm$^2$, thereby depositing copper microparticles 9. In this case, as shown in FIG. 7, anode plates 14 are placed so as to face in parallel to the surface, onto which copper microparticles 9 are formed, of the drum foil 6.

In the seal-plating bath 13B for preventing release of the copper microparticles 9, a copper sulfate solution (sulfuric acid concentration of 150 g/l, copper concentration of 65 g/l, temperature 45° C.) is employed, and electroplating is carried out for 20 seconds under conditions for level plating and at a current density of 15 A/dm$^2$. In this case, as shown in FIG. 7, anode plates 14 are placed such that the anodes plates face in parallel to the copper-microparticles (9)-deposited surface of the drum foil 6.

Anti-corrosion treatment is carried out in an anti-corrosion-treatment bath 15, by use of zinc serving as a corrosion-inhibiting element. The zinc concentration in the anti-corrosion-treatment bath 15 is maintained by employing a soluble anode 16 formed of a zinc plate. The electroplating is carried out in a concentration-constant zinc sulfate solution comprising sulfuric acid (70 g/l) and zinc (20 g/l), for 10 seconds at a temperature of 40° C. and a current density of 15 A/dm$^2$.

After completion of the anti-corrosion treatment, the drum foil 6 is passed through, over 40 seconds, a drying portion 17 where the atmosphere had been adjusted to 110° C. by means of an electric heater. The thus-dried surface-treated copper foil is then wound into a roll, to thereby produce the S-HTE copper foil 1 having a foil thickness of 18 μm. During the aforementioned steps, the drum foil 6 runs at 2.0 m/minute in the surface-treatment apparatus 11. A rinsing bath 18 capable of performing about 15 sec. water-rinsing is arranged between successive operation baths, thereby preventing the solution from being carried over from the previous bath.

Sheets of the thus-produced S-HTE copper foil 1 and a sheet of CEM-3 substrate having a thickness of 150 μm were laminated, to thereby produce double-sided copper-clad laminate specimens (30 cm×30 cm). Evaluation of bow, twist, and dimensional stability of the specimens was performed through the following methods.

Bow and twist of the double-sided copper-clad laminate specimens were evaluated by placing each specimen, without applying any load, on a level block of high flatness. The bow was evaluated in accordance with JIS C-6481, 5.22. The specimen was placed on the level block such that the convex side of the specimen was the upper side. The maximum distance from the upper side of the level block was measured. The bow ratio was calculated from the following formula:

$$\text{Bow ratio } (\%) = (H/L) \times 100;$$

wherein L represents the width of the copper-clad laminate specimen placed on the level block and H represents the maximum distance measured from the upper side of the level block.

Twist was evaluated in accordance with IPC-TM-650, 2.4.22. The specimen was placed on the level block of high flatness such that the convex side of the specimen was the upper side and three of four corners remained in contact with the level block under application of a load. The maximum distance between the remaining corner and the surface of the level block was measured. The twist ratio was calculated from the following formula:

$$\text{Twist ratio } (\%) = (D/L) \times 100;$$

wherein L represents the diagonal distance of the specimen placed on the level block and D represents the maximum distance between the remaining corner and the surface of the level block.

Dimensional stability was evaluated in accordance with JIS C6481, 5.16. In practice, the specimen (30 cm×30 cm) was drilled to form a reference hole at each corner thereof such that the interval between two adjacent holes was 250 mm. After the specimen had been allowed to stand for 24 hours in an atmosphere of 20° C. and a relative humidity of 60–70%, the distance ($l_0$) between two arbitrary adjacent holes was measured. Subsequently, both copper foil layers of the specimen were removed by etching, and the specimen was dried at 80° C. for 15 minutes. After the specimen had been allowed to stand for one hour in an atmosphere of 20° C. and a relative humidity of 60–70%, the distance ($l_1$) between two arbitrary adjacent holes was measured. By use of $l_1$, the dimensional change due to etching was calculated. In addition, the etched specimen was heated at 170° C. for 0.5 hours. After the specimen had been allowed to stand for 1 hour in an atmosphere of 20° C. and a relative humidity of 60–70%, the distance ($l_2$) between two arbitrary adjacent holes was measured. By use of $l_2$, the dimensional change due to heating was calculated. The following formulas were employed to calculate dimensional stability:

[Dimension change ratio after etching (%)]=$(l_0-l_1)/l_0 \times 100$;

and

[Dimension change ratio after heating (%)]=$(l_0-l_2)/l_0 \times 100$.

TABLE 1

| Bow ratio (%) | | 1.0 | |
|---|---|---|---|
| Twist ratio (%) | | 0.5 | |
| Dimensional stability (%) | After etching | MD: 0.007 | TD: 0.005 |
| | After heating | MD: 0.030 | TD: 0.010 |

MD:Measured in the machine direction of rolling of electrodeposited copper foil during production.
TD:Measured in a direction normal to the machine direction (MD); i.e., in a transverse direction.

COMPARATIVE EXAMPLE

The procedure of Example was repeated, except that the elctrolyte employed in the electroforming step A was not subjected to activated-carbon treatment, to thereby produce an electrodeposited copper foil having a thickness of 18 μm and to evaluate the properties thereof. Repeated description of details of the procedure is simplified or omitted. The results of evaluation are shown in Table 2.

TABLE 2

| Bow ratio (%) | | 5.0 | |
|---|---|---|---|
| Twist ratio (%) | | 3.2 | |
| Dimensional stability (%) | After etching | MD: 0.063 | TD: 0.034 |
| | After heating | MD: 0.108 | TD: 0.057 |

MD:Measured in the machine direction of rolling of electrodeposited copper foil during production.
TD:Measured in a direction normal to the machine direction (MD); i.e., in a transverse direction.

As is clear from Tables 1 and 2, the values in Table 1, showing the results of evaluation of copper-clad laminates employing the electrodeposited copper foil of the present invention, are lower than those in Table 2. In addition, each value shown in Table 1 is satisfactory for a copper-clad laminate produced through employment of the S-THE copper foil according to the present invention. The results indicate that bow and twist of copper-clad laminates can be reduced and that the dimensional stability thereof can be improved by employing the S-HTE copper foil according to the present invention without carrying out cumbersome additional steps.

EFFECTS OF THE INVENTION

By employing, in a printed circuit board, a copper-clad laminate produced through employment of the S-HTE copper foil according to the present invention, bow and twist of the laminate can be reduced and the dimensional stability thereof can be improved. Reduction of bow and twist results in uniform adhesion between a resist and the copper foil surface. Thus, uniform light exposure can be provided on the applied resist, thereby readily producing finer circuits. Through improvement of the dimensional stability of a copper-clad laminate, interlayer matching for producing a multi-layer printed wiring board can easily be performed. This is advantageous particularly in a mass-lamination method and a build-up method.

What is claimed is:

1. An electrodeposited copper foil providing improved bow and twist and dimensional stability to copper-clad laminates which: recrystallizes by heating at low temperature during production of a copper-clad laminate employing an electrodeposited copper foil; and exhibits an elongation as high as 18% or more in an atmosphere at 180° C., comprising selecting those copper foils wherein
    the maximum rate of decrease in maximum tensile strength falls within an aging time ranging from 5 to 10 minutes during aging in an atmosphere at 170° C., and
    the change in tensile strength in a knick portion shown in a {tensile strength}vs. {aging time}curve drawn in an x–y plane is 3 kg/mm² or more.

2. A method of selecting an electrodeposited copper foil of claim 1, comprising
    cutting an electrodeposit copper foil and preparing two strip specimens having dimensions of 1 cm×10 cm;
    subjecting one specimen to aging at 170° C. for 5 minutes and the other specimens to aging at 170° C. for 10 minutes.
    subsequently cooling the specimens to room temperature;
    subsequently mounting each specimen in a tensile tester;
    applying a tensile force at a rod speed of 10 mm/minute; and
    measuring the maximum tensile strength of each specimen so as to confirm that the difference between the two values is 3 kg/mm² or more.

3. A copper-clad laminate employing an electrodeposited copper foil as recited in claim 1.

* * * * *

UNITED STATES PATENT AND TRADEMARK OFFICE
CERTIFICATE OF CORRECTION

PATENT NO.    : 6,479,170 B1  
DATED         : November 12, 2002  
INVENTOR(S)   : Takahashi et al.

It is certified that error appears in the above-identified patent and that said Letters Patent is hereby corrected as shown below:

<u>Column 12,</u>  
Line 38, after the word "other", the word "specimens" should be -- specimen --.

Signed and Sealed this

Twenty-fifth Day of March, 2003

JAMES E. ROGAN  
*Director of the United States Patent and Trademark Office*